US00PP32828P2

(12) United States Plant Patent
Trees et al.

(10) Patent No.: US PP32,828 P2
(45) Date of Patent: Feb. 23, 2021

(54) ***LANTANA* PLANT NAMED 'PURPLE FALLS'**

(50) Latin Name: *Lantana montevidensis*
Varietal Denomination: Purple Falls

(71) Applicant: Ball Horticultural Company, West Chicago, IL (US)

(72) Inventors: Scott C. Trees, Arroyo Grande, CA (US); Colleen N. Konkler, Nipomo, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 16/884,224

(22) Filed: May 27, 2020

(51) Int. Cl.
*A01H 5/02* (2018.01)
*A01H 6/86* (2018.01)

(52) U.S. Cl.
USPC ..... Plt./227

(58) Field of Classification Search
USPC ..... Plt./226, 227
See application file for complete search history.

*Primary Examiner* — Susan McCormick Ewoldt
*Assistant Examiner* — Karen M Redden
(74) *Attorney, Agent, or Firm* — Audrey Charles

(57) ABSTRACT

A new and distinct cultivar of *Lantana* plant named 'Purple Falls', characterized by its medium purple-colored flowers, dark green-colored foliage, and vigorous, mounded-trailing growth habit, is disclosed.

1 Drawing Sheet

Latin name of genus and species of plant claimed: *Lantana montevidensis.*

Variety denomination: 'Purple Falls'.

BACKGROUND OF THE INVENTION

The present invention relates to a new and distinct cultivar of *Lantana* plant botanically known as *Lantana montevidensis* and hereinafter referred to by the cultivar name 'Purple Falls'.

The new cultivar originated in a controlled breeding program in Guadalupe, Calif. during June 2016. The objective of the breeding program was the development of *Lantana* cultivars with a vigorous, mounded-trailing growth habit.

The new *Lantana* cultivar is the result of cross-pollination and embryo rescue. The female (seed) parent of the new cultivar is 'Trailing Lavender', not patented, characterized by its medium lavender-colored inflorescences, medium green-colored foliage, and vigorous, mounded-trailing growth habit. The male (pollen) parent of the new cultivar is the proprietary *Lantana montevidensis* breeding selection coded 4197-1, not patented, characterized by its dark lavender-colored flowers, dark green-colored foliage, and vigorous, trailing growth habit. The new cultivar was selected as a single flowering plant within the progeny of the above stated cross-pollination during January 2017 in a controlled environment in Guadalupe, Calif.

Asexual reproduction of the new cultivar by terminal stem cuttings since January 2017 in Guadalupe, Calif. and Arroyo Grande, Calif. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Purple Falls' as a new and distinct cultivar of *Lantana* plant:

1. Medium purple-colored flowers;
2. Dark green-colored foliage; and
3. Vigorous, mounded-trailing growth habit.

Plants of the new cultivar differ from plants of the female parent primarily in having darker purple-colored flowers at the fully opened stage of development and darker green-colored foliage. Plants of the new cultivar differ from plants of the male parent primarily in having a more mounded-trailing growth habit.

Of the many commercially available *Lantana* cultivars, the most similar in comparison to the new cultivar is 'Purple Trailing', not patented. However, in side-by-side comparisons, plants of the new cultivar differ from plants of 'Purple Trailing' in at least the following characteristics:

1. Plants of the new cultivar have more growth vigor than plants of 'Purple Trailing'; and
2. Plants of the new cultivar have more branches per plant than plants of 'Purple Trailing'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Purple Falls'. The approximately 4-month-old plants were grown in 4.5-inch pots for approximately 2 weeks, then transplanted into 6-inch pots and grown for an additional 12 weeks in a greenhouse in West Chicago, Ill. Plants were given one pinch one week after the first transplant.

DETAILED BOTANICAL DESCRIPTION

Figure 1:
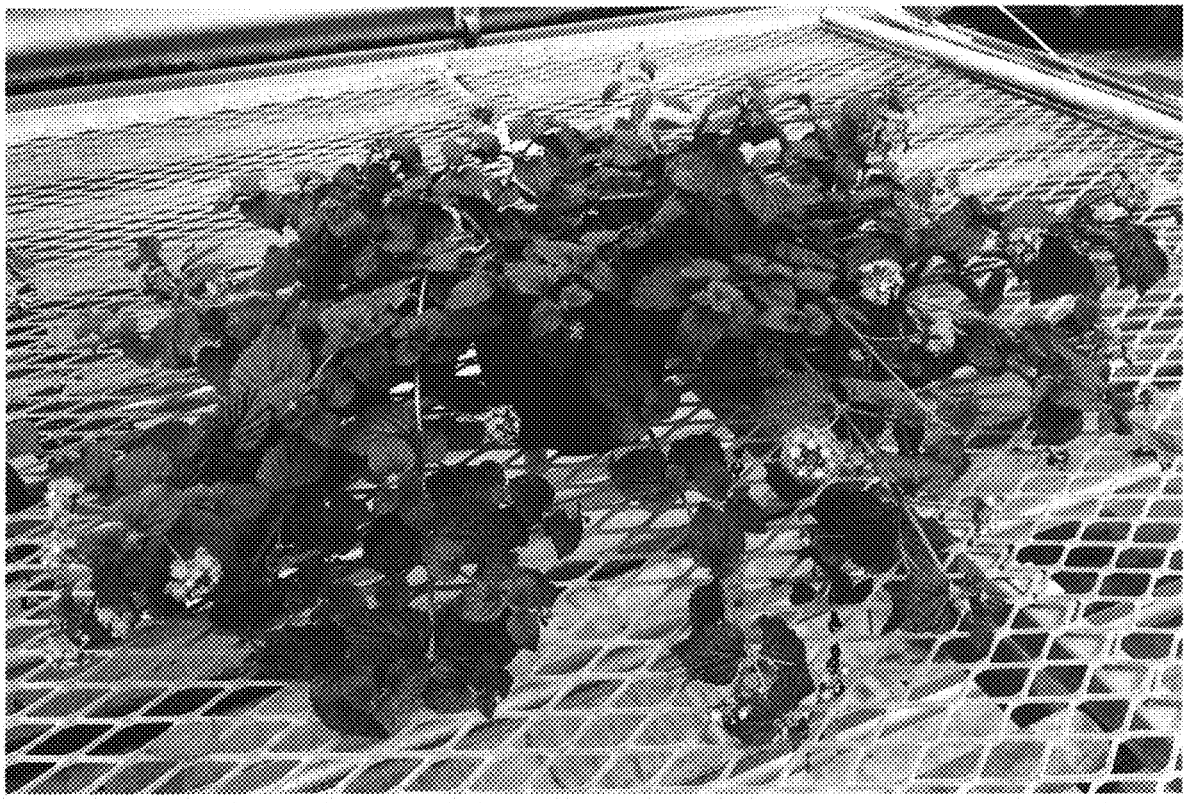
FIG. 1 illustrates a side view of the overall growth and flowering habit of 'Purple Falls'.
Figure 2:
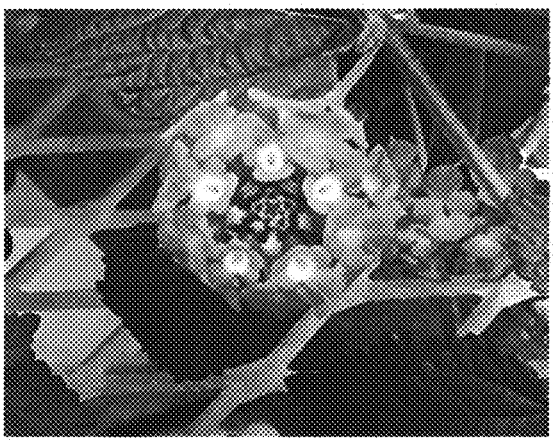
FIG. 2 illustrates a close-up view of an individual inflorescence of 'Purple Falls'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in May 2020 under natural light conditions in West Chicago, Ill.

The following descriptions and measurements describe approximately 4-month-old plants produced from cuttings from stock plants and grown in a glass-covered greenhouse under conditions comparable to those used in commercial practice. The plants were grown in West Chicago, Ill. utilizing a soilless growth medium in 4.5-inch pots for approximately 2 weeks, then transplanted into 6-inch pots and grown for an additional 12 weeks. Plants were given one pinch one week after the first transplant. Greenhouse temperatures were maintained at approximately 67° F. to 72° F. (19° C. to 22° C.) during the day and approximately 65° F. to 68° F. (18° C. to 20° C.) during the night. Supplemental lighting was used. Measurements and numerical values represent averages of typical plants.

Botanical classification: *Lantana montevidensis* 'Purple Falls'.

Parentage:

*Female parent.*—'Trailing Lavender', not patented.

*Male parent.*—*Lantana montevidensis* breeding selection coded 4197-1, not patented.

Propagation:

*Type cutting.*—Terminal stem.

*Time to initiate roots.*—Approximately 7 to 11 days.

*Time to produce a rooted cutting.*—Approximately 28 to 35 days.

*Root description.*—Fibrous.

*Rooting habit.*—Freely branching.

Plant description:

*Commercial crop time.*—Approximately 7 to 8 weeks from a rooted cutting to finish in a 15 cm pot.

*Growth habit and general appearance.*—Vigorous, mounded-trailing,

*Size.*—Height from soil level to top of plant plane: Approximately 13.0 cm. Width: Approximately 90.0 cm.

*Branching habit.*—Freely branching, pinching enhances branching. Quantity of lateral branches per plant: Approximately 5.

*Branch.*—Shape: Square in cross section. Strength: Strong, becomes woody with age. Length: Approximately 44.0 cm. Diameter: Approximately 3.0 mm. Length of central internode: Approximately 5.5 cm. Texture: Densely pubescent with a mixture of glandular and nonglandular hairs. Gland color: Colorless, transparent. Color of young stem: 144A. Color of mature stem: 146B becoming woody 199B with age.

Foliage description:

*General description.*—Quantity of leaves per lateral branch: Approximately 18. Fragrance: Strong, spicy. Form: Simple. Arrangement: Opposite.

*Leaves.*—Aspect: Perpendicular to obtuse angle to stem. Shape: Ovate. Margin: Serrate. Apex: Acute. Base: Obtuse. Venation pattern: Pinnate. Length of mature leaf: Approximately 5.2 cm. Width of mature leaf: Approximately 4.1 cm. Texture of upper surface: Scabrous. Texture of lower surface: Scabrous and glandular pubescent. Gland color: 1D, transparent. Color of upper surface of young foliage: 137A with venation of 146B to indistinguishable. Color of lower surface of young and mature foliage: Closest to between 138A and 138B with venation of 146C. Color of upper surface of mature foliage: Closest to NN137A with 139A, venation of 146B to indistinguishable.

*Petiole.*—Length: Approximately 4.0 mm. Diameter: Approximately 2.0 mm. Texture: Scabrous and glandular pubescent. Gland color: 1D, transparent. Color: 146B.

Flowering description:

*Flowering habit.*—'Purple Falls' is freely flowering under outdoor growing conditions with substantially continuous blooming from spring through autumn and year-round in greenhouse environment.

*Lastingness of individual inflorescence on the plant.*—Approximately 2 to 3 weeks.

Inflorescence description:

*General description.*—Type: Hemispherical head, axillary or terminal. Quantity per plant: Approximately 40. Fragrance: Mild, spicy. Aspect: Facing upward or outward. Height: Approximately 1.2 cm. Width: Approximately 2.4 cm. Quantity of fully open flowers per inflorescence: Approximately 16.

*Peduncle.*—Strength: Strong. Shape: Square in cross section. Aspect: Acute angle to stem. Length: Approximately 4.3 cm. Diameter: Approximately 1.0 mm. Texture: Scabrous and glandular pubescent. Gland color: Colorless, transparent. Color: 146B.

Flower description:

*General description.*—Type: Salverform.

*Bud.*—Rate of opening: Generally takes 1 to 2 days for bud to progress from first color to fully open flower. Buds open in progression from the margin to the center of the inflorescence. Quantity of unopened inflorescences per plant: Approximately 60.

*Bud just before opening.*—Shape: Elongated, rectangular at apex. Length: Approximately 6.0 mm. Diameter: Approximately 1.5 mm. Color: N81D.

*Corolla.*—Depth: Approximately 1.0 cm. Diameter: Approximately 9.0 mm.

*Petals.*—Quantity: 4, non-imbricate, non-symmetrical petals. Petals are fused at base forming a corolla tube. Shape: Obovate. Appearance: Dull. Aspect: Cupped, flattens somewhat with age. Margin: Entire to erose, slightly wavy. Apex: Obtuse. Length of upper petal from throat: Approximately 3.0 mm. Width of upper petal: Approximately 6.0 mm. Length of lateral petals from throat: Approximately 3.0 mm. Width of lateral petals: Approximately 4.0 mm. Length of lower petal from throat: Approximately 5.0 mm. Width of lower petal: Approximately 6.0 mm. Texture of upper surface: Glabrous. Texture of lower surface: Moderately pubescent, mixture of hairs and glands. Gland color: Colorless, transparent. Color of upper surface when first open: N81C with lower petal of N81B, bases of N155D and 7A at throat opening. Color of lower surface when first open: N155D tinted with N81B to N81C. Color of upper surface when fully open: N81C with lower petal of N81B, bases of N155A tinted with N81B to N81C. Color of lower surface when fully open: N155D tinted with N81C.

*Corolla tube.*—Length: Approximately 8.0 mm. Diameter at tube opening: Approximately 1.0 mm. Diameter at base: Approximately 1.0 mm. Texture of inner surface: Sparsely pubescent. Texture of outer surface: Densely pubescent with a mixture of glandular and nonglandular hairs at tube opening transitioning to glabrous at base. Pubescence color: Colorless, transparent. Color of inner surface: NN155D. Color of outer surface: NN155D with an overlay of N81B located on distal two thirds.

*Calyx.*—Shape: Tubular with two broadly acute tips. Length: Approximately 2.0 mm. Diameter: Approximately 1.0 mm. Texture of inner surface: Glabrous. Texture of outer surface: Densely pubescent with a mixture of glandular and nonglandular hairs. Gland color: Colorless, transparent. Color of inner and outer surfaces: 154D.

*Bracts.*—Quantity per flower: 1 per flower. Shape: Ovate. Apex: Acute. Base: Obtuse. Length: Approximately 6.0 mm. Width: Approximately 3.0 mm. Texture of upper surface: Sparsely pubescent, mixture of hairs and glands. Texture of lower surface: Moderately pubescent, mixture of hairs and glands. Gland color: 1D. Color of upper surface: 137A with 145B at base. Color of lower surface: 137D with 145B at base.

*Reproductive organs.*—Androecium: Stamen quantity: 4, adnate to corolla tube. Stamen length: Approximately 1.5 mm. Anther shape: Bilobed, ovoid. Anther length: Approximately 1 mm. Anther color: 7A. Pollen amount: Moderate. Pollen Color: 7D. Gynoecium: Pistil quantity: 1 per flower. Pistil length: Approximately 3.0 mm. Stigma shape: Funnel. Stigma length: Less than 1 mm. Stigma color: Closest to 144A. Style length: Approximately 2.0 mm. Style color: Colorless, translucent. Ovary diameter: Approximately 1.0 mm. Ovary color: Closest to 144D.

Seed and fruit production: Neither seed nor fruit production has been observed.

Disease and pest resistance: Resistance to pathogens and pests common to *Lantana* has not been observed.

What is claimed is:

1. A new and distinct cultivar of *Lantana* plant named 'Purple Falls', substantially as herein illustrated and described.

* * * * *